United States Patent [19]

Haber et al.

[11] Patent Number: 5,372,586
[45] Date of Patent: Dec. 13, 1994

[54] TELESCOPING PHARMACEUTICAL STORAGE AND MIXING SYRINGE

[75] Inventors: Terry M. Haber, Lake Forest; William H. Smedley, Lake Elsinore; Clark B. Foster, Laguna Niguel, all of Calif.

[73] Assignee: Habley Medical Technology Corp., Laguna Hills, Calif.

[21] Appl. No.: 139,586

[22] Filed: Oct. 20, 1993

[51] Int. Cl.[5] ............... A61M 37/00; A61M 5/00
[52] U.S. Cl. .................... 604/89; 604/91; 604/191
[58] Field of Search .......... 604/187, 191, 198, 263, 604/89, 91

[56] References Cited

U.S. PATENT DOCUMENTS

| | | | |
|---|---|---|---|
| 2,841,145 | 7/1958 | Epps | 604/89 |
| 3,477,432 | 11/1969 | Shaw | 604/91 |
| 3,680,558 | 8/1972 | Kapelowitz | 604/89 |
| 4,563,174 | 1/1986 | Dupont et al. | 604/89 |
| 5,067,948 | 11/1991 | Haber et al. | |
| 5,114,411 | 5/1992 | Haber et al. | |
| 5,147,323 | 9/1992 | Haber et al. | |
| 5,211,285 | 5/1993 | Haber et al. | |
| 5,240,146 | 8/1993 | Smedley et al. | |
| 5,281,198 | 1/1994 | Haber et al. | |

FOREIGN PATENT DOCUMENTS 2229374 9/1990 United Kingdom ............... 604/191

Primary Examiner—John D. Yasko
Assistant Examiner—Adam J. Cermak
Attorney, Agent, or Firm—Townsend & Townsend Khourie & Crew

[57] ABSTRACT

A unitary syringe assembly including a diluent syringe and a jell syringe stores and enables convenient transport of isolated components required for injection. A valve is placed between the two syringes. Immediately before required injection, the valve is opened and the diluent and jell between the two syringes are thoroughly intermixed. Valve aperture size is selected to provide viscous resistance to the flow of the jell until thorough mixing has occurred to provide the user with a tactile indication of sufficient mixing. Upon complete mixing, a needle is attached and injection occurs.

10 Claims, 3 Drawing Sheets

TELESCOPING PHARMACEUTICAL STORAGE AND MIXING SYRINGE

This invention relates to syringes. More particularly, a syringe construction is shown provides for isolated transport of a jell and a diluent in separate measured and isolated quantities to avoid the otherwise short shelf life of the jell/diluent mixture. The separate cylinders fasten together as a coaxial unitary assembly and are interconnected by a valve which enables mixing of the jell and diluent immediately before injection. The resultant diluent/jell mixture does not require handling either outside of the syringes or manipulation of separate syringes relative to a special mixing appliance.

BACKGROUND OF THE INVENTION

Certain pharmaceuticals for injection must be stored and transported in a jell format. Unfortunately, these pharmaceuticals in the jell format are too viscous for direct injection. Some of these jells are utilized in chemotherapy.

A preferred jell here used would comprise a cytotoxant and a bulking agent. A preferred low viscosity diluent would comprise a vaso-constricting agent. The jell or high viscosity factor contains a cytotoxin mixed with a biocompatible bulking agent. The diluent or lower viscosity factor comprises a vaso-constrictor to inhibit blood supply to the tumor.

Presence of the bulking agent structures stabilizes the location of the implant within the tumor so as to retain the most effective positioning for the most protracted time period possible. Unfortunately, this effect is of short duration. Thus mixing is required immediately prior to injection. By way of example, a common injected dosage included 9 cc of jell with 0.9 cc of diluent.

The present solution to this problem is to package, store and ship the diluent in one syringe and the jell in another syringe. Immediately before injection, the two separate syringes are opened and connected to a mixing manifold. Thereafter, fluid flow to and from each syringe occurs. Finally, when proper mixing has occurred, substantially all of the mixed jell and diluent is injected to one syringe—for example the syringe that originally transported the jell. Thereafter, injection conventionally occurs.

The manipulation of two separate glass syringes to a separate fitting immediately prior to injection is burdensome and unduly complex for the modern medical environment. What is needed is a unitary assembly which is self contained and user friendly to the required mixing.

In our Haber et al. U.S. Pat. No. 5,211,285 issued May 18, 1993 entitled Telescoping Pharmaceutical Mixing Container, we addressed the problem of the storage and transport of NPH insulin. Simply stated, insulin crystals separate out from carrying fluid during storage. In this disclosure, a smaller inner cylinder and a larger outer cylinder were telescoped and communicated by an apertured plug on the bottom of the smaller inner cylinder. The larger cylinder was closed by a needle piercing septum. The smaller inner cylinder was closed at the proximal end immediate apertured plug by a floating piston forming an air spring with the closed end of the small cylinder.

Mixing occurred by the expedient of leaving the needle piercing septum in place. The small cylinder and apertured plug were depressed into the large cylinder. This depression occurred against the floating piston and air spring of the small cylinder. Air in the air spring was compressed by the floating piston allowing agitating and mixing fluid movement occurred between the small and large cylinders through the apertured plug. When this agitating movement between the large and small cylinder accomplished complete mixing, the needle septum of the large cylinder is ruptured with a needle and the small cylinder depressed. Injection occurs under force of the air spring by depression of the small cylinder into the large cylinder.

This device is not suitable for solution to the present problem of adding diluent to a jell. First, it does not provide for the separate and isolated storage of the medical components. Second, and because injection occurs against the back pressure provided by an air spring, it is suitable for shallow injection only of fluids that are of relatively low viscosity.

As distinguished from this application, the exemplary jell mixed with diluent provides a more complex mixing and injection environment. Isolation of the jell and diluent is required during transport and storage. Further, provision must be made for occasional deep injection, sometimes with needles up to seven inches in length. Such injections cannot occur against the force provided by an air spring.

SUMMARY OF THE INVENTION

A unitary syringe assembly including a diluent syringe and a jell syringe stores and enables convenient transport of isolated components required for injection. A valve is placed between the two syringes. Immediately before required injection, the valve is opened and the diluent and jell between the two syringes are thoroughly intermixed. Valve aperture size is selected to provide viscous resistance to the flow of the jell until thorough mixing has occurred to provide the user with a tactile indication of sufficient mixing. Upon complete mixing, a needle is attached and injection occurs.

DESCRIPTION OF THE PREFERRED EMBODIMENT

In the following description herein, an outline will be followed. The main elements of the embodiment will first be summarily identified. Thereafter, a detailed description of each of these elements will be made—with major reference to the exploded view provided herewith. Finally, operation will be set forth. This operation will be discussed first with respect to the loading for transport and storage of the syringes here shown and secondly with use of the syringe assembly for mixture and usual injection.

Figure 1:
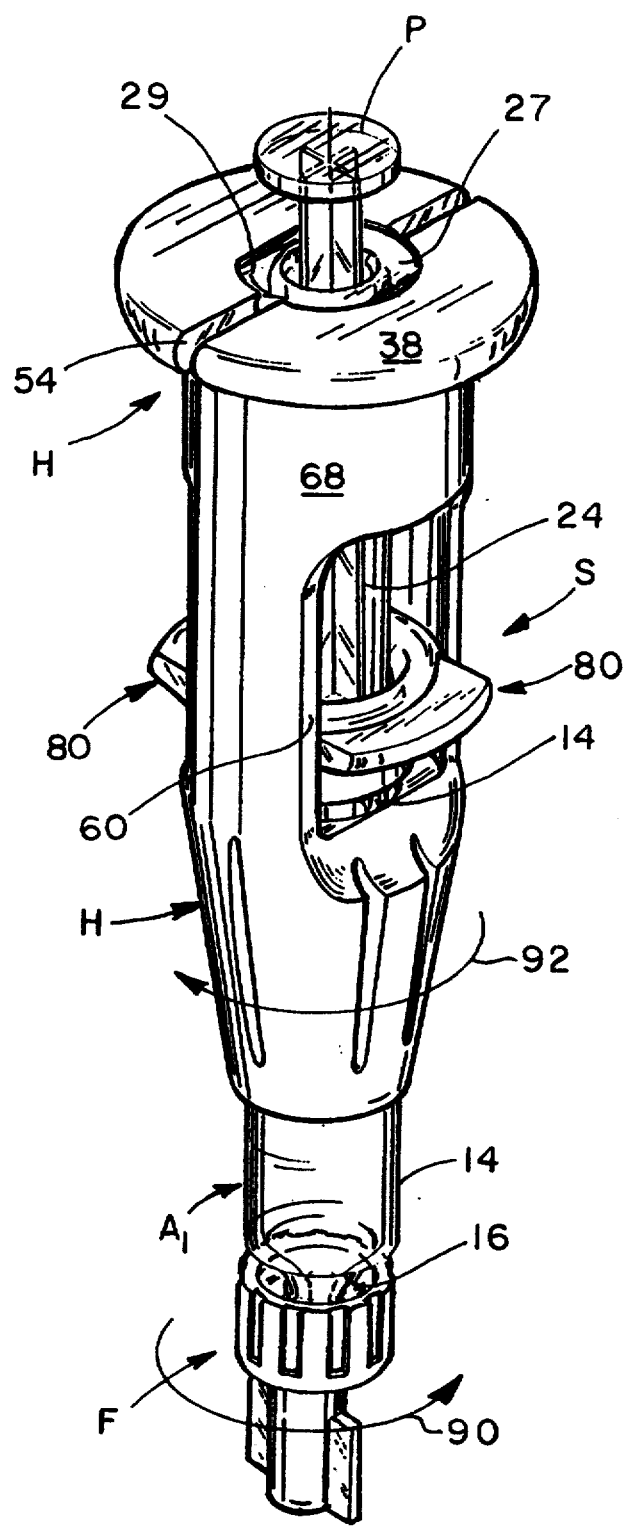
FIG. 1 is a perspective assembled view of a unitary syringe assembly utilizing coaxial inner and outer syringes interconnected at an isolation valve for jell/diluent isolation upon transport and storage and intermixture of the jell/diluent immediately prior to needle attachment for injection at the illustrated needle fitting.
Figure 2:
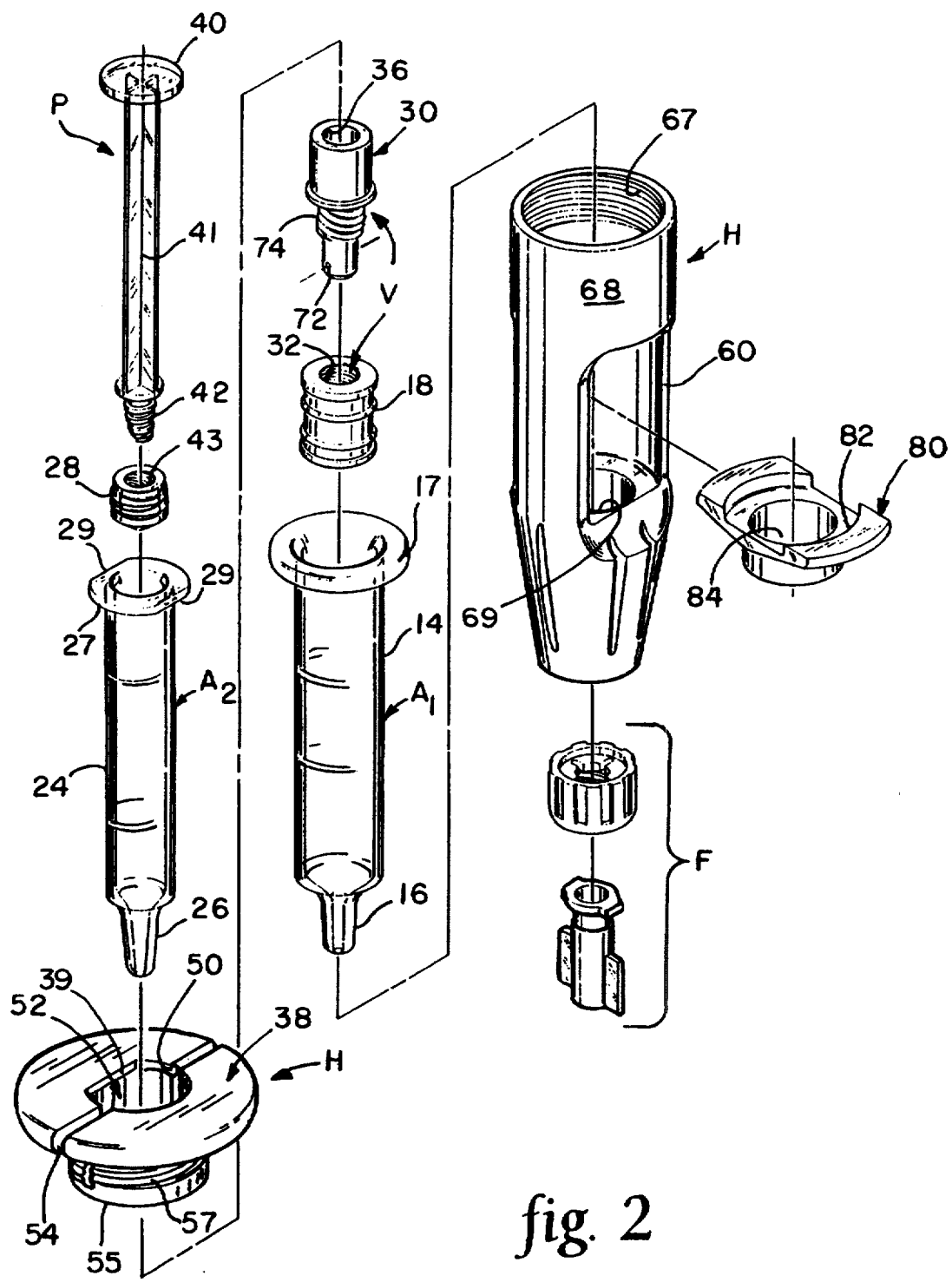
FIG. 2 is a perspective exploded view of the components of the assembled unitary syringe assembly of FIG. 1.
Figure 3:
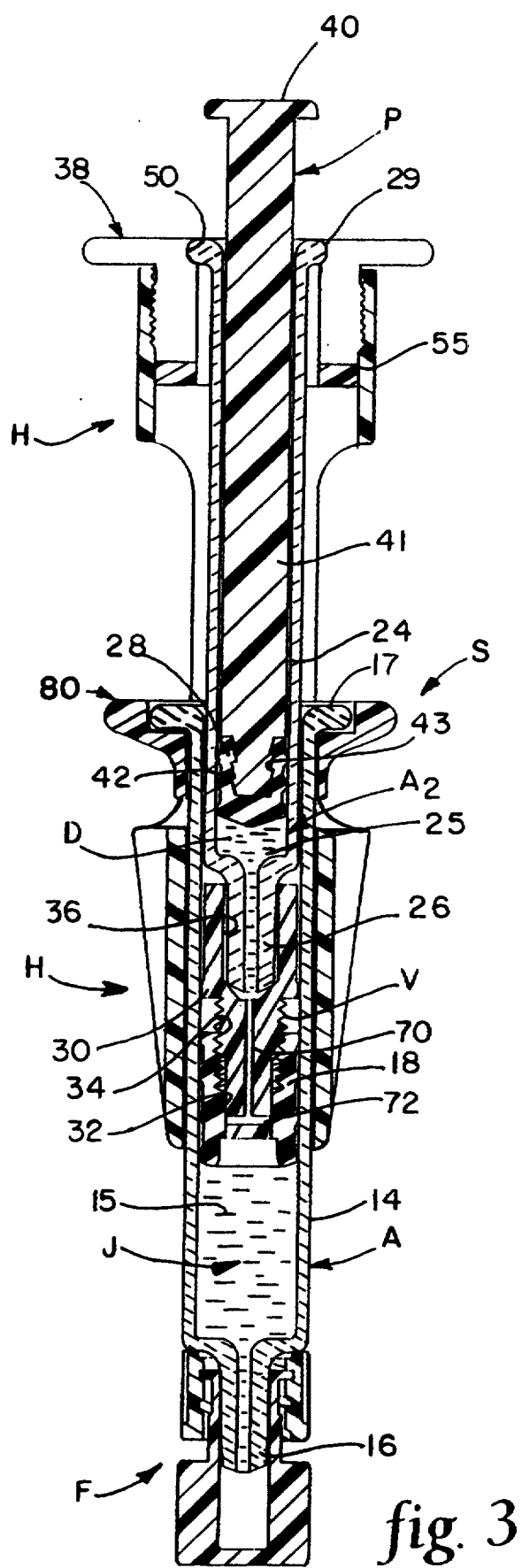
FIG. 3 is a cross section of the embodiment of FIG. 1 illustrating the isolated jell and diluent storage and transport compartments and displaying the isolation valve so that its operation upon relative rotation of the inner and outer syringes for communication of jell and diluent can be understood.

With respect to FIGS. 1 and 3, unitary syringe S of the first embodiment is illustrated. Referring briefly to FIGS. 2 and 3, first syringe assembly $A_1$ having jell containing volume J is illustrated. Second syringe assembly $A_2$ having diluent containing volume D is shown.

First syringe assembly $A_1$ includes cylinder 14, cylinder outlet 16 and sealing piston 18. Second syringe assembly $A_2$ includes cylinder 24, cylinder outlet 26, and sealing piston 28.

First piston 18 in syringe assembly $A_1$ is displaced by coaxial syringe assembly $A_2$ through a valve assembly V. Second piston 28 in syringe assembly $A_2$ is displaced by plunger P. It will be more completely understood that the respective syringe assemblies $A_1$, $A_2$ are mounted coaxially within a common housing H.

Because the jell 15 and diluent 25 are required to be stored and transported in isolation one from another, it is required that a valve V separate the two substances. This valve assembly V here includes a plastic adaptor 30 fixed to syringe assembly $A_2$ at the outlet 26 and a bore 32 within piston 18 of first syringe assembly $A_1$. As will hereafter be more clearly set forth, once plastic adaptor 30 moves longitudinally down bore 32, communication through valve V will occur, permitting jell 15 to be mixed with diluent 25.

Finally, there is mounted a fitting F for dispensing the mixed jell 15 and diluent 25. In the case of utilizing syringe S for injection through a needle, fitting F constitutes a standard Leur fitting for the attachment of a needle—the needle not being shown.

Having set forth the main operative components, the detailed construction of these components will be set forth with primary reference to the exploded view of FIG. 2 and reference when necessary to FIGS. 1 and 3.

Plunger P includes a digit depressing flange 40 at the top, stem member 41, and male plunger thread 42 at the bottom. Male plunger thread 42 engages female plunger thread 43, fastening piston 28 to plunger P.

Cylinder 24 of syringe assembly $A_2$ includes an upper flange section 27 having two linear edges 29. One of these linear edges 29 fits to a corresponding linear edge 39 in cap section 38.

Cap section 38 of housing H is relatively easy to understand. It includes a central aperture 52 bounded by a concave annulus (see FIG. 3). This concave annulus 50 receives flange sections 27, 29 of second syringe assembly $A_2$. As will more clearly appear hereafter, second syringe assembly $A_2$ is not free to rotate relative to housing H.

Cap section 38 is slotted at slot 54 which terminates just before base 55. Cap section 38 included external male threads 57 which mate with female threads 67 and housing section 68. In assembly, the two halves of cap section 38 are deflected radially outwardly from slot 54 to receive flange section 27 of second syringe assembly $A_2$ with edges 29, 39 adjacent one another. Thereafter, flange section 27 is firmly captured interior of central aperture 52 by concave annulus 50 when cap section 38 is threaded onto housing section 68 at threads 67.

Plastic adaptor 30 fastens permanently to the exterior of outlet 26 of second syringe assembly $A_2$ at bore 36. Adapter 30 includes a central bore 70 ending in a T at cross bore 72. Valve assembly V is maintained in the closed position by having cross bore 72 sealed at bore 32 of sealing piston 18. Plastic adaptor 30 further includes male threads 74 which mate with threads 34 interior of sealing piston 18.

As will hereafter be set forth, when syringe assembly $A_1$ is rotated relative to syringe assembly $A_2$, engagement between threads 34 and 74 occurs. This causes crossbore 72 to clear the bottom of bore 32 in sealing piston 18 opening communication between the respective syringe assemblies $A_1$ and $A_2$ for the required mixing.

Cylinder 14 of syringe assembly $A_1$ includes flange 17. Flange 17 fits interior first syringe assembly handle 80 at annulus 82 while hole 84 in handle 80 passes around the exterior of first syringe assembly $A_1$. First syringe assembly handle 80 protrudes from the sides of housing section 68 at windows 60.

Housing section 68 receives cylinder 14 of first syringe assembly $A_1$. Outlet 16 of first syringe assembly $A_1$ fits through aperture 69 of housing section 68. Thereafter, state of the art Luer lock fitting F is fastened about outlet 16 effectively sealing first syringe assembly $A_1$.

Having described in pertinent portion the detailed construction of syringe S, attention will now be devoted to assembly of the syringe with jell 15 and diluent 25 for storage and transport.

First syringe assembly $A_1$ with fitting F sealing the bottom and housing H attached is first loaded with jell 15. Thereafter, sealing piston 18 is seated relative to jell 15.

Second syringe assembly $A_2$ with plastic adaptor 30 is seated with respect to sealing piston 18 and male threads 74 of plastic adaptor 30 only started in engagement with female threads 34 of sealing piston 18. Such partial threading occludes crossbore 72 maintaining valve V in the closed position.

Second syringe assembly $A_2$ with cap section 38 attached is then charged with diluent 25. Piston 28 is seated overlying diluent 25 typically by the well known "wine cork" method. Once such seating has occurred, plunger P is secured to piston 28, assembly is essentially complete. Cap section 38 is seated in housing section 68 with threads 57, 67 being engaged.

Operation of the transported and stored unit may now be set forth.

Referring to FIG. 1, the user will typically grasp housing H in one hand and the outer portion of first syringe assembly $A_1$ in the other hand. Such grasping will occur at the lower section of first syringe assembly $A_1$ at fitting F and cylinder 14. First syringe assembly $A_1$ will be rotated in the direction 90 relative to housing H in the direction 92. Opening of valve V will occur by crossbore 72 in plastic adaptor 30 clearing bore 32 of piston 18. This movement occurs because the friction between piston 18 and the inner of cylinder 14 is greater than the friction between threads 34, 74. A fluid passage from the interior of first syringe assembly $A_1$ through central bore 70 and crossbore 72 of plastic adaptor 30 will open to second syringe assembly $A_2$.

Thereafter, plunger P and first syringe assembly handle 80 (in window 60 of housing section 68) will alternately be depressed toward cap section 38 of housing H. Movement of plunger P downward will cause handle section 80 to move downward. Conversely, movement of handle section 80 upwardly toward cap section 38 will cause plunger P to move upward. These motions will be repeated until thorough mixing occurs.

Central bore 70 and crossbore 72 of plastic adaptor 30 are sized to give the user a tactile clue as to the thoroughness of mixing. The first stroke of plunger P will expel diluent 25 into jell 15. Immediately thereafter, partially mixed jell 15, in trying to pass through central bores 70 and crossbore 72, will only pass with some difficulty because of viscous resistance within the bores. As mixing progresses, such movement will occur with greater ease—this being sensed by the effort required to move handle 80 and plunger P relative to housing H. Thus, thorough mixing can be observed through the transparent wall of syringe assembly $A_1$ and will be tactually apparent by the resistance to mixing.

Finally, when mixing is complete, a needle will be mounted to fitting F. Thereafter plunger P will be depressed. No matter what particular portion of the intermixed diluent 25 and jell 15 is in either syringe assembly $A_1$ or $A_2$, expulsion of the intermixed contents will occur.

It is to be noted that injection without intermixture will not occur. Jell 15 is too viscous to admit of injection through a needle without the required mixture.

What is claimed is:

1. A unitary syringe assembly for the isolated storage and transport of two substances with intermixed injection of said two substances comprising:
    a first syringe assembly for containing a first of said two substances, said syringe assembly including a cylinder defining an interior, a cylinder outlet, and a sealing piston for sealing said first substance within said first syringe assembly;
    means for displacing said sealing piston of said first syringe to cause substances in said first syringe to be likewise displaced out said cylinder outlet;
    a second syringe assembly coaxial to said first syringe assembly for containing a second of said two substances, said syringe assembly including a cylinder defining an interior, cylinder outlet, and sealing piston for sealing said second substance within said second syringe assembly;
    means for displacing said sealing piston of said second syringe to cause substances in said second syringe to be likewise displaced out said cylinder outlet;
    a common housing, said first and second syringe assemblies being mounted relative to one another in the common housing;
    an isolation valve fluidly coupling the cylinder outlet of one said syringe assembly with the interior of the other of said syringe assemblies when in an open condition and fluidly isolating said cylinder outlet of said one syringe assembly from said interior of said other syringe assembly when in a closed condition; and,
    a dispensing head fitting mounted to the outlet of said other syringe assembly to permit the contents of at least said other syringe assembly to be dispensed through a dispensing head responsive to movement of at least one of said means for displacing.

2. The unitary syringe assembly of claim 1 and wherein:
    said piston of one of said syringe assemblies acts as a seat for said isolation valve.

3. A unitary syringe assembly according to claim 2 and wherein:
    said isolation valve includes a portion of one of said pistons; and
    means on one of said pistons for moving said piston upon relative rotation of one of said coaxial cylinders to the other of said coaxial cylinders to open communication between said first and second syringe assemblies.

4. A unitary syringe assembly according to claim 1 and wherein:
    said dispensing head fitting includes means for mounting a needle for injection of said intermixed substances to a patient.

5. A unitary syringe assembly according to claim 2 and wherein:
    said isolation valve includes,
    a first relatively moving member fixedly mounted to said one syringe assembly;
    a second relatively moving member formed into said piston of said other piston assembly; and,
    means for relatively moving said cylinder of said first and second syringe assemblies to enable said relatively moving members of said isolation valve to move between said closed condition where said substances are isolated and the open condition where said substances are communicated.

6. The unitary syringe assembly of claim 5 and wherein:
    said second relatively moving member includes a passage communicating to said cylinder outlet of said first syringe assembly at one end and to a side of said first relatively moving member at an opposite end, said second relatively moving member defining second threads for permitting relative movement between said first and second relatively moving members;
    said first relatively moving member includes complementary first threads for engagement with the second threads to enable said opposite end of said passage to be obstructed in said closed condition and to provide communication to said second syringe in said open condition.

7. A unitary syringe assembly loaded with two substances for the isolated storage and transport of said two substances with intermixed injection of said two substances comprising:
    a first syringe assembly for containing a first of said two substances, said syringe assembly including a cylinder defining an interior, cylinder outlet, and sealing piston for sealing said first substance within said first syringe assembly;
    one of said two substances loaded in said first syringe assembly between said sealing piston and said cylinder outlet;
    means for displacing said sealing piston of said first syringe to cause said substance in said first syringe to be likewise displaced out said cylinder outlet;
    a second syringe assembly coaxial to said first syringe assembly for containing a second of said two substances, said syringe assembly including a cylinder defining an interior, cylinder outlet, and sealing piston for sealing said second substance within said second syringe assembly;
    the other of said two substances loaded in said second syringe assembly between said sealing piston and said cylinder outlet;
    means for displacing said sealing piston of said second syringe to cause substance in said second syringe to be likewise displaced out said cylinder outlet;
    a common housing, said first and second syringe assemblies being mounted relative to one another in the common housing;
    an isolation valve fluidly coupling the cylinder outlet of one said syringe assembly with the interior of the other of said syringe assemblies when in an open condition and fluidly isolating said cylinder outlet of said one syringe assembly from said interior of said other syringe assembly when in a closed condition; and, a dispensing head fitting mounted to the outlet of said other syringe assembly to permit the contents of at least said other syringe assembly to be dispensed through a dispensing head responsive to movement of at least one of said means for displacing.

8. A unitary syringe assembly loaded with two substances according to claim 7 and wherein: one of said substances is a jell and the other of said substances is a diluent for said jell.

9. A unitary syringe assembly loaded with two substances according to claim 8 and wherein:

said jell includes a cytotoxant and a bulking agent; and, said diluent comprises a vaso-constricting agent.

10. A unitary syringe assembly loaded with two substances according to claim 8 wherein:

said isolation valve includes means for providing the user with a tactile indication of the degree of mixing of the jell and diluent.

* * * * *